United States Patent
Criswell (10) Patent No.: US 9,555,407 B2
(45) Date of Patent: Jan. 31, 2017

(54) LASER TRIANGULATION FOR PIPETTE TIP POSITION

(71) Applicant: Protedyne Corporation, Windsor, CT (US)

(72) Inventor: Victor Criswell, Southbury, CT (US)

(73) Assignee: Protedyne Corporation, Windsor, CT (US)

( * ) Notice: Subject to any disclaimer, the term of this patent is extended or adjusted under 35 U.S.C. 154(b) by 488 days.

(21) Appl. No.: 13/828,750

(22) Filed: Mar. 14, 2013

(65) Prior Publication Data
US 2014/0260696 A1    Sep. 18, 2014

(51) Int. Cl.
*B01L 3/02*    (2006.01)
*G01N 35/10*   (2006.01)

(52) U.S. Cl.
CPC ......... *B01L 3/021* (2013.01); *G01N 35/1011* (2013.01)

(58) Field of Classification Search
CPC ....... B01L 3/021; B01L 3/0217; B01L 3/0275; B01L 2200/0689; Y10T 436/2575
USPC ............. 73/864.01, 863.31, 864.22, 864.23, 73/864.24
See application file for complete search history.

(56) References Cited

U.S. PATENT DOCUMENTS

| | | | |
|---|---|---|---|
| 6,088,106 A | 7/2000 | Röckseisen | |
| 6,132,582 A | 10/2000 | King et al. | |
| 6,288,786 B1 | 9/2001 | Rudd et al. | |
| 7,429,360 B2 | 9/2008 | Kureshy et al. | |
| 7,876,935 B2 | 1/2011 | Massaro | |
| 2003/0111494 A1 | 6/2003 | Lin et al. | |
| 2004/0023223 A1 | 2/2004 | Thompson et al. | |
| 2005/0124059 A1* | 6/2005 | Kureshy et al. | ........... 435/287.2 |
| 2005/0136534 A1 | 6/2005 | Austin et al. | |
| 2006/0085162 A1 | 4/2006 | Bjornson et al. | |
| 2007/0177778 A1* | 8/2007 | Massaro | ........... 382/128 |
| 2008/0060719 A1 | 3/2008 | Massaro | |
| 2011/0035848 A1 | 2/2011 | Perkins et al. | |

FOREIGN PATENT DOCUMENTS

WO    WO 2012/069925 A1    5/2012

OTHER PUBLICATIONS

Guo et al., Extraction of Depth Information and Image Processing in Manipulator Cell Injection, Micronanoelectronic Technology, Nov. 2007, pp. 1012-1016, MEMS Device & Technology.
International Search Report and Written Opinion for PCT/US2014/020980, mailed Jun. 26, 2014 (13 pages).
França, J.G., et al., A 3D Scanning System Based on Laser Triangulation and Variable Field of View, IEEE, 2005.
Peiravi, A. et al., A Reliable 3D Laser Triangulation-based Scanner with a New Simple but Accurate Procedure for Finding Scanner Parameters, Journal of American Science, 2010, pp. 80-85, vol. 6, issue 5, Marsland Press.

* cited by examiner

*Primary Examiner* — Eric S McCall
*Assistant Examiner* — Mohammed E Keramet-Amircolai
(74) *Attorney, Agent, or Firm* — Kilpatrick Townsend & Stockton LLP (57) ABSTRACT

A sample processing apparatus includes a laser triangulation system that locates the position of a lower end of a pipette tip. When the laser triangulation system identifies a discrepancy between the actual position of the lower end and the proper position of the lower end, the sample processing apparatus may undergo a compensating action to compensate for the discrepancy.

20 Claims, 7 Drawing Sheets

LASER TRIANGULATION FOR PIPETTE TIP POSITION

BACKGROUND

1. Field

This invention relates to a sample processing apparatus with a laser triangulation system for pipette tip position.

2. Discussion of Related Art

Sample processing apparatus are used to automatically manipulate sample holders and precise amounts of fluid. These devices enable testing and analysis of samples in many fields, such as genomics, drug discovery, proteomics, and diagnostics.

SUMMARY

According to one aspect, a method for determining pipette tip position includes attaching a pipette tip to a pipetting head. The pipette tip has a lower end that extends away from the pipetting head. The method also includes using laser triangulation to locate a position of the lower end of the pipette tip, and compensating for the position of the lower end with a compensating action.

According to another aspect, a sample handling apparatus includes a pipetting head that is adapted to hold a pipette tip and allow for movement of a liquid sample relative to the pipette tip. The pipette tip has a lower end. The sample handling apparatus also includes a laser triangulation system that is constructed and arranged to locate a position of the lower end of the pipette tip relative to the pipetting head. Finally, the sample handling apparatus also includes a controller that is constructed and arranged to calculate the position of the lower end of the pipette tip relative to the pipetting head. The controller is also constructed and arranged to operate the pipetting head to perform a compensating action to compensate for the position of the lower end of the pipette.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Sample processing apparatuses are used to manipulate fluid samples so that various sample handling operations may be performed using the samples, such as aspirating, dispensing, centrifuge processing, mixing, filtering and electrophoretic gel separation. Such sample handling operations may be performed using a pipetting head and pipette tips. These sample handling operations may be performed automatically and concurrently on a plurality of samples, enabling high throughput and rapid testing protocols.

The inventors have recognized that some pipette tips may be formed with defects due to tolerances and/or errors involved in the pipette tip manufacturing process. For example, a pipette tip may be slightly crooked or slanted, giving rise to a lower end that is offset from the longitudinal axis of the pipette tip. Pipette tip defects may give rise to inaccuracies that may cause contamination, errors, and inaccurate results during sample handling operations.

According to one aspect, laser triangulation is used to locate the position of the lower end of a pipette tip relative to a pipetting head, and a compensating action is performed to compensate for irregularities or deformities of the pipette tip in order to proceed with a sample handling operation.

Figure 1:
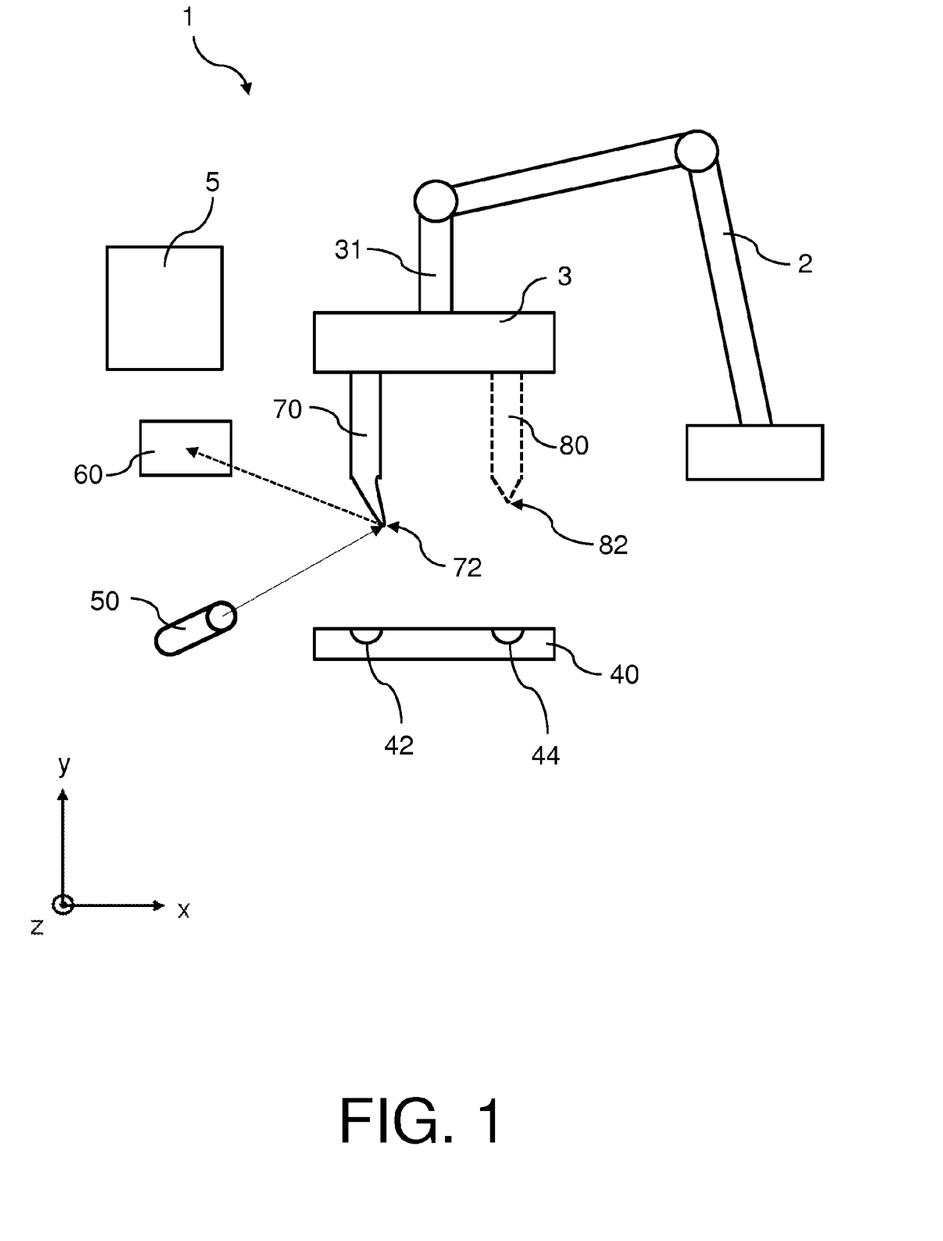
FIG. 1 is a side view of a sample processing apparatus according to one embodiment.

As shown in FIG. 1, a sample processing apparatus 1 according to one embodiment includes a first pipette tip 70 that is attached to a pipetting head 3. First pipette tip 70 has a deformed lower end 72, as the lower end 72 is offset from the longitudinal axis of the pipette tip 70. The pipetting head 3 may also be attached to a second pipette tip 80. As shown in FIG. 1, the second pipette tip 80 has a normal lower end 82 that is aligned with the longitudinal axis of pipette tip 80. As used herein, the term "lower end" refers to the end of the pipette tip opposite to the end that attaches to the pipetting head. The "lower end" may refer to the extreme end point of the pipette tip, or the immediate vicinity thereof. The "lower end" may include the lowermost inlet/outlet opening through which fluid passes in and out of the pipette tip. Precise positioning of the lower end is crucial for accurate dispensing of fluids into openings of vessels such as wells of a well-plate, for aspiration of fluids out of such vessels, and for any other fluid handling operation that requires alignment of the pipette tip with a target. For example, during dispensing of fluid from the pipette tip, the position of the lower end of the pipette tip determines where fluid falls. As shown in FIG. 1, second pipette tip 80 has a normal lower end 82 that is aligned with the longitudinal axis of the pipette tip 80. Lower end 82 is properly positioned such that it is aligned with second well 44 of well plate 40. In contrast, deformed lower end 72 is misaligned with the first well 42 of well plate 40. If fluid is dispensed from the first pipette tip 70 down towards the well plate 40 when the lower end 72 is in the position depicted in FIG. 1, at least some fluid will fall outside of first well 42 and may lead to contamination of other wells and surrounding components.

The sample handling apparatus includes a laser triangulation system that locates the precise position of the lower ends of pipette tips relative to a reference point. In some embodiments, the reference point is located on the pipetting head, such that the position of the lower end is calculated relative to the pipetting head. In some embodiments, the reference point is attached to the work surface on which the pipetting head and robotic manipulator are situated. The laser triangulation system may include one or more laser sources 50 and one or more detectors 60. As shown in FIG. 1, the laser source 50 illuminates the lower end 72 of the first pipette tip 70, and the position of the illumination is detected by detector 60. Information regarding the position of the illumination is sent to a controller 5, which calculates the position of the lower end 72 of the pipette tip 70 relative to a reference point such as a point on the pipetting head 3. The controller 5 may control the operation of laser source 50 and detector 60, for example, turning detector and laser source 50 or off, controlling the timing and/or power of the laser source 50, and controlling the position and orientation of the laser source 50 and detector 60. The controller 5 may also control operation of the pipetting head 3 as well. The controller 5 may command the pipetting head 3 to conduct a sample handling operation such as, but not limited to, dispensing or aspirating a fluid, to eject a pipette tip, or to disable liquid handling operation of a specific pipette tip. Communication between controller 5 and the portions of the sample handling apparatus 1 such as the laser source 50, detector 60, and pipetting head 3 maybe via wired and/or wireless communication. As will be discussed below, the controller 5 may also control operation of the robotic manipulator 2.

In some embodiments, the laser source 50 and detector 60 may be combined into a single instrument. The laser source and detector may be located within a single housing. In other embodiments, the laser source and detector are separated.

The detector 60 may be a simple photon-detecting sensor, such as a photodiode, a CCD array, a camera, any suitable image acquisition device, any device suitable for capturing an image using visible or other electromagnetic radiation, or any other suitable detector for sensing laser illumination, as this aspect is not limited in this regard. The detector 60 may be capable of capturing images in rapid succession to record a movie clip, and/or may be capable of capturing still images or simply the presence or existence of laser light at a location.

The laser source 50 may use red laser light, green laser light, blue laser light, or any other suitable laser wavelength, as this aspect is not limited in this regard. The laser source 50 may be a moderate-power laser, a high-power laser, or have any other suitable power rating, as this aspect is not limited in this regard.

In some embodiments, the pipetting head only attaches to one pipette tip at a time. In some embodiments, the pipetting head 3 may attach to a second pipette tip 80. In some embodiments, the pipetting head 3 may be attachable to multiple pipette tips at a time, but may be operated to attach to only one pipette tip at a time. The pipetting head 3 may attach to any number of pipette tips at a time, as this aspect is not so limited.

Where more than one pipette tip is attached to the pipetting head, in one embodiment, a second laser source may be used to illuminate the lower end 82 of the second pipette tip 80. In some cases, a second detector may be used to detect the position of the illumination. In other cases, the same detector 60 may be used to detect the illumination of the first lower end 72 and the second lower end 82. In some cases, a single laser source 50 is used to illuminate both lower ends 72, 82, while a single detector is used to detect the illumination of the lower ends 72, 82. In some embodiments, detection of lower ends 72, 82 may occur simultaneously or substantially simultaneously. In other embodiments, detection of lower ends 72, 82 may be spaced in time.

In some embodiments, however, only one pipette tip 70 is attached to pipetting head 3. In other embodiments, two or more pipette tips may be attached to the pipetting head, and any suitable laser triangulation system may be used to locate the position of the lower ends of the pipette tips.

The pipetting head 3 may be arranged to support and/or actuate one, some or all of the pipette tips, such that the tips can be moved together from a first position to a second position and actuated to aspirate and/or dispense a liquid sample. The pipetting head 3 may itself be manipulated by a robotic manipulator 2 or other arrangement that is adapted to support, move and/or actuate the pipetting head 3.

Figure 2:
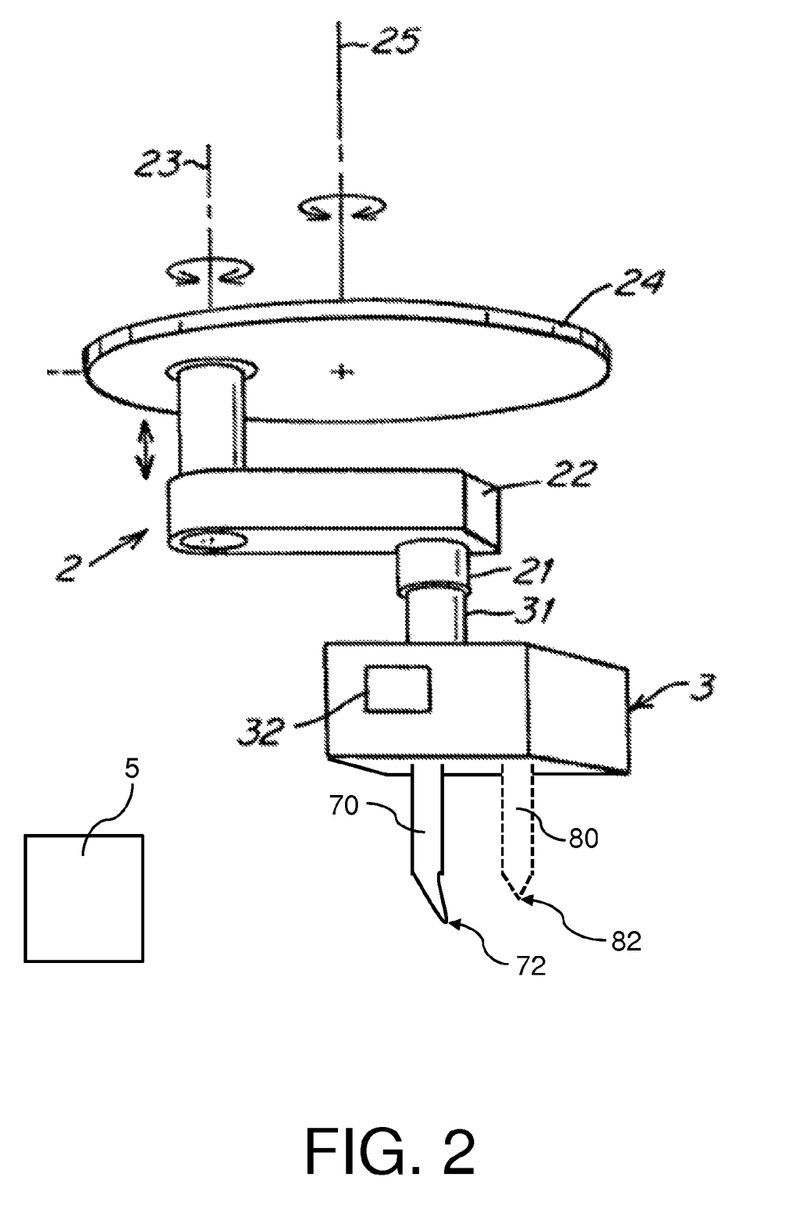
FIG. 2 is a perspective view of a robotic manipulator according to one embodiment.

The robotic manipulator 2 may include a Cartesian robot, SCARA-type robot, and/or any other type of robot having any suitable number of degrees of freedom. FIG. 2 shows an illustrative embodiment of a robotic manipulator 2. In this illustrative embodiment, the robotic manipulator 2 is a SCARA-type robot (like that described in U.S. Pat. No. 7,374,525, filed Jan. 25, 2006, which is hereby incorporated by reference in its entirety) which includes an arm 22 that may be rotated about an axis 23 and moved linearly along the axis 23 relative to a turntable 24, which may itself be rotated about an axis 25. The robotic manipulator 2 may be adapted to pick up and drop two or more tools such as a pipetting head 3, a gripping tool (e.g., for picking and placing multiwell plates or other sample holders), tools for performing optical or other analysis of liquid samples in sample holders, and/or tools for performing other liquid sample handling tasks or operations. The robotic manipulator 2 may include a coupling 21 that allows the device 2 to removably engage with a tool 3, which may itself have a corresponding coupling 31. The couplings 21 and 31 may allow for mechanical engagement between the robotic manipulator 2 and the tool 3 as well as provide electrical, optical, pneumatic, hydraulic and/or other connections to provide power and/or control signals to the tool 3. Power and/or control signals provided to the tool 3 may be generated by a system controller 5, which may also function to control operation of the robotic manipulator 2 and/or other portions of the sample handling apparatus 1. Control signals provided to the tool 3 may be in any form, and may be acted on by the tool 3 in any way. For example, the system controller 5 may provide low level control signals to the tool 3 that define explicit control instructions. Alternately, or in addition, the system controller 5 may provide higher level instructions to a tool controller 32 on the tool 3, which may decode the high level instructions, and generate lower level control signals for one or more portions of the tool 3 to perform the function(s) called for by the system controller 5. In one embodiment, the tool controller 32 may store instructions provided by the system controller 5, and use the stored instructions for later liquid sample handling operations performed while disconnected from the robotic manipulator 2. For example, the system controller 5 may provide instructions to the tool controller 32 to perform one or more tasks with respect to liquid samples held by the tool 3 once the tool 3 is disconnected from the robotic manipulator 2. The tools 3 may also send information to the system controller 5, e.g., regarding position feedback, the processing status of an associated liquid sample or set of samples and/or other information. Communication between the tools 3 and system controller 5 may be via wired and/or wireless connection, e.g., tools 3 may communicate wirelessly with the system controller 5 while disconnected from the robotic manipulator 2 and on a support.

Any suitable laser triangulation and/or LIDAR method and system may be used to locate the position of the lower end of the pipette tip, as this aspect is not limited in this regard. Any suitable number of laser sources and detectors may be used, and any suitable positioning of such laser sources and detectors may be used as well. In some embodiments, the laser source(s) may be held stationary, while in other embodiments, the laser source(s) may move. In some embodiments, the detector(s) may be held stationary, while in other embodiments, the detector(s) may move.

The laser triangulation system may be used with tools other than pipette tips. For example, if a gripping tool is connected to a robotic manipulator, laser triangulation may be used to verify functionality or determine the geometry of the gripping tool. As one example, laser triangulation may be used to locate the relative positions of the opposing arms of the gripping tool to determine whether the arms are closing properly. As another example, laser triangulation may be used to determine whether the opposing arms are deformed or have any irregularities. Laser triangulation can be used to determine the shape and position of various tools. Such information can be used to determine, for example, whether the tool needs to be replaced or repaired, or whether the tool needs to be re-aligned with a certain target.

Figure 3:
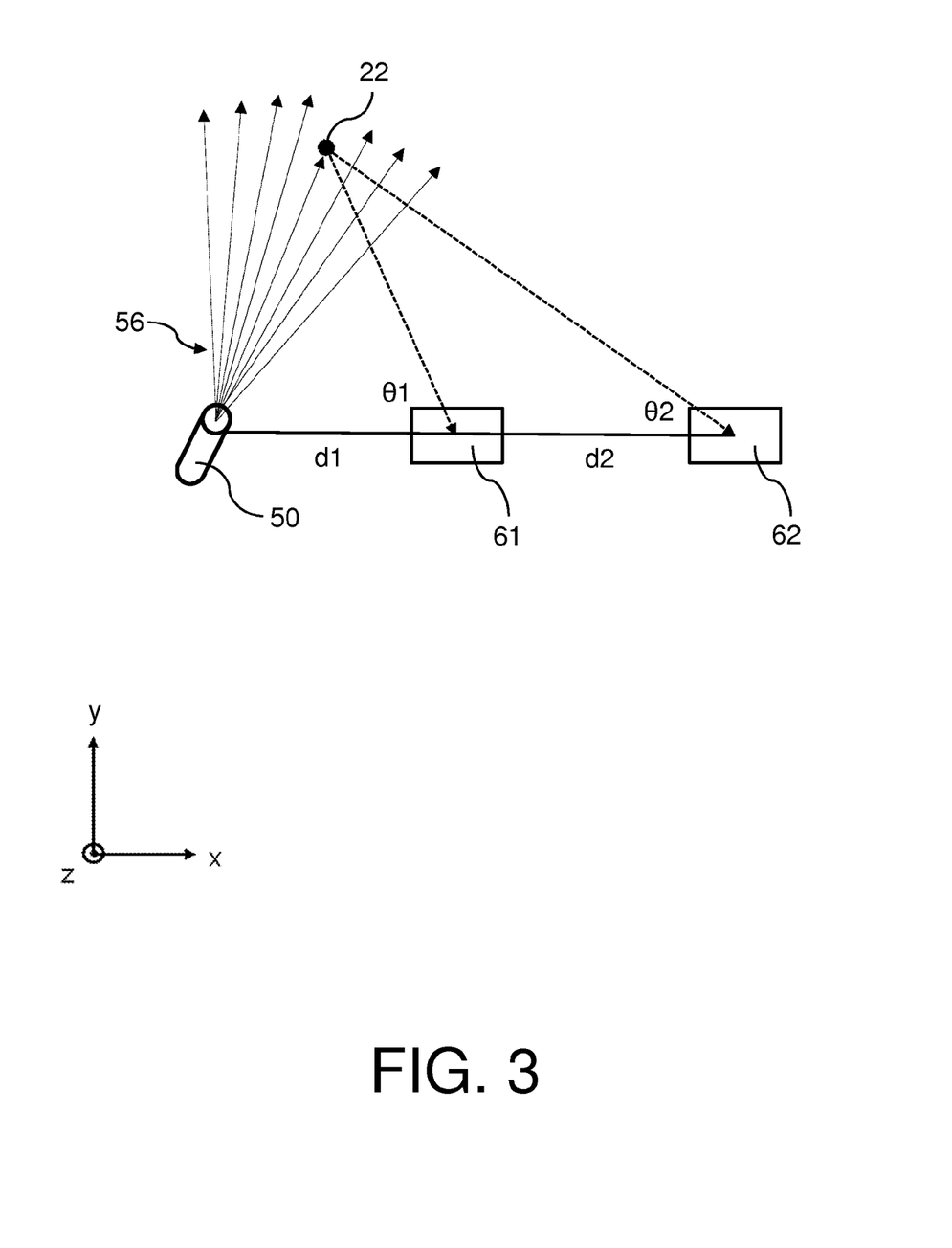
FIG. 3 is a top view of a laser triangulation system according to one embodiment.

In one illustrative embodiment, as shown in FIG. 3, where the z-axis height of the lower end 22 of a pipette tip is approximately known, a laser triangulation system may use a single laser source 50 and two detectors 61, 62 to locate the lower end 22 of the pipette tip. The distance d1 between the laser source 50 and the first detector 61 is pre-set and known, as is the distance d2 between the first detector 61 and the second detector 62. The laser source 50, and detectors 61, 62 are held stationary, though their orientations and/or positions may be adjusted if needed. The laser source 50 may project a fan 56 or a plane of laser light that spreads over the x-y plane at the z-axis height of the lower end 22, hitting and illuminating the lower end 22 of the pipette tip. Angles $\theta 1$ and $\theta 2$ are determined during detection of the illumination of the lower end 22 by first and second detectors 61, 62. With angles $\theta 1$ and $\theta 2$ known and distances d1, d2 also known, the x, y position of the lower end 22 can be determined using trigonometric relationships. The values of $\theta 1$, $\theta 2$, d1 and d2 may be sent to a controller, which calculates the x, y position of lower end 22 relative to a reference point, such as a point on the pipetting head 3.

Although the laser source 50 and detectors 61, 62 are collinear in FIG. 3, as long as the relative distances and positions between the three components are known, each component may be positioned in any manner. For example, the laser source 50 may be positioned between the first and second detectors 61, 62. The laser source 50 and detectors 61, 62 may be non-collinear. The laser source 50 and detectors 61, 62 may be part of a single instrument such that they are positioned within a common housing, or they may be separate components.

Figure 4:
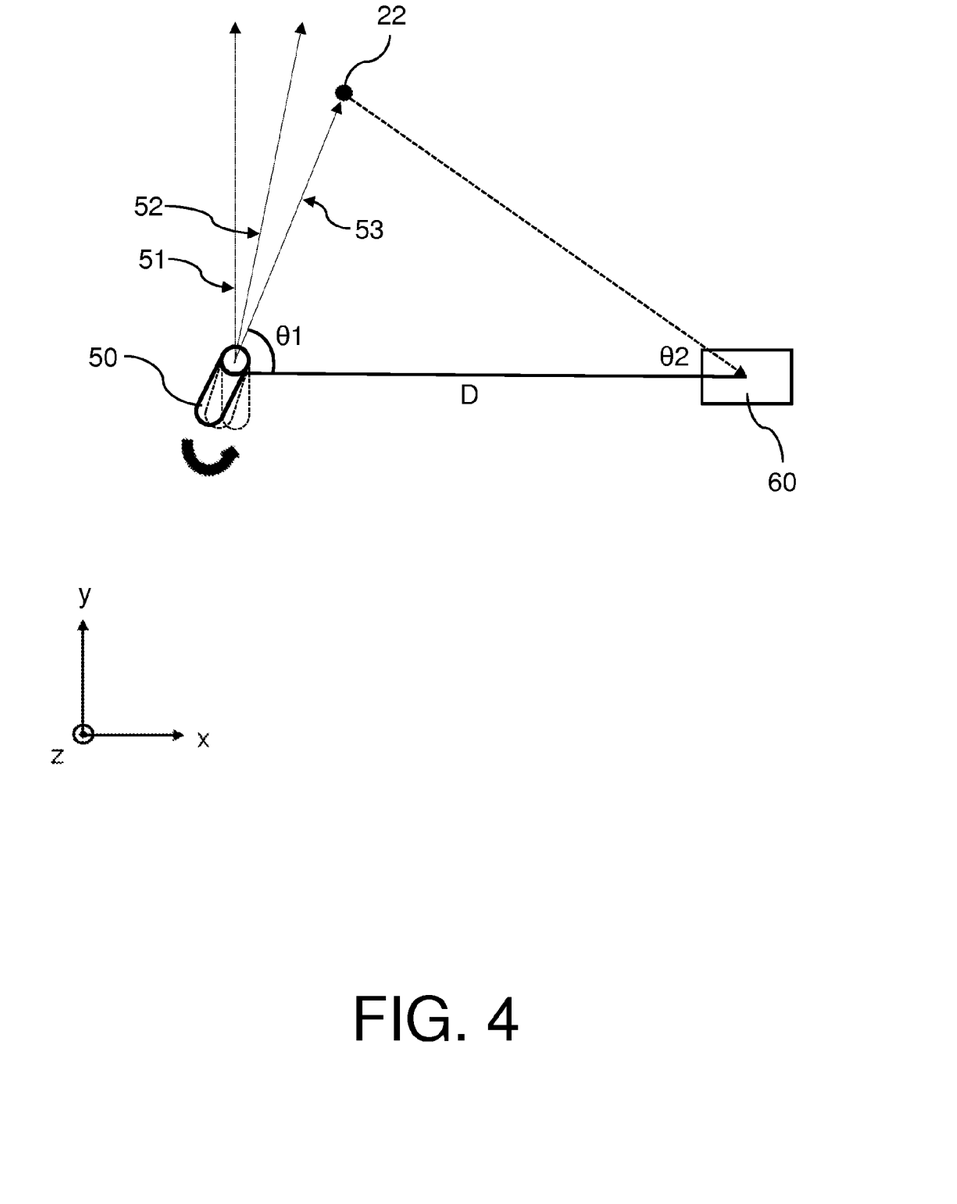
FIG. 4 is a top view of another laser triangulation system according to one embodiment.

In another illustrative embodiment, shown in FIG. 4, where the z-axis height of the lower end 22 of a pipette tip is approximately known, a laser triangulation system may use a single laser source 50 and a single detector 60 to locate the lower end 22 of a pipette tip. The distance D between the laser source 50 and the detector 60 is pre-set and known. Laser source 50 is controlled to pivot through an angle, projecting a laser beam at each angle. (As will be understood, the entire source 50 device need not be pivoted, but rather a laser beam may be scanned, such as by a pivoting or rotating mirror, the angular position of which may be known and used to determine the illumination angle.) Laser source 50 starts at a first angle to emit beam 51, rotates to a second angle to emit beam 52, then rotates to a third angle $\theta 1$ to emit beam 53, which hits and illuminates the lower end 22 of the pipette tip. As such, $\theta 1$ is the angle of illumination. Illumination of the lower end 22 is detected by detector 60. A controller, which monitors the angle of the laser source 50 and while receiving communication signals from the detector 60, pairs the timing of the illumination detection event with the angle of the laser source 50, and thus determines the angle of illumination $\theta 1$. Angle $\theta 2$ is determined during detection of the illumination of the lower end 22 by the detector 60. With angles $\theta 1$ and $\theta 2$ known and distance D also known, the x, y position of the lower end 22 can be determined using trigonometric relationships. The values of $\theta 1$, $\theta 2$, and D may be sent to a controller, which calculates the x-y position of lower end 22 relative to a reference point, such as a point on the pipetting head 3.

In some embodiments, the 3-dimensional position (x, y, and z coordinates) of the lower end of a pipette tip may be determined. In one embodiment, a robotic manipulator may be combined with a laser triangulation system to determine the x, y, and z coordinates of the lower end of a pipette tip. In one embodiment, shown in FIG. 5, a laser triangulation system may include a single laser source 50 and two detectors 61, 62. Laser source 50 may be a stationary laser source that emits a plane of laser light 58 at a constant z-axis height. The robotic manipulator 2 may position the pipetting head 3 such that the pipette 70 and lower end 72 are positioned well above the plane of light 58. The robotic manipulator may then translate the pipetting head downward in the z-direction toward the plane of laser light 58. Since the lower end 72 of pipette 70 is the lowermost surface of pipette 70, downward movement of the pipette 70 will cause the lower end 72 to contact the plane of laser light 58 first. Once the plane of laser light 58 intersects with the lower end 72, the lower end 72 is illuminated, and the illumination is detected by detectors 61, 62. Once illumination is detected, the controller 5 may command the robotic manipulator 2 to discontinue downward translation, thereby maintaining the z-axis height of illumination. Since the orientation and position of the robotic manipulator 2 is known, the z-axis height of the lower end 72 can be determined. In some embodiments, the system acts as a type of laser trip wire, where, once illumination is detected, downward translation of the pipetting head 3 is paused and the z-axis height is maintained while the x, y position of the lower end 72 is determined. With the z-axis height of the lower end 72 known and the lower end 72 illuminated, determination of the x, y position of the lower end 72 can be determined in the same manner as that discussed in the illustrative embodiment depicted in FIG. 3. In some embodiments, the system stores data on the fly and need not "pause" at the z-axis height of illumination. In some embodiments, the system is able to detect illumination and calculate the x, y, and z coordinates so quickly that no pause at the z-axis height of illumination is needed.

Figure 5:
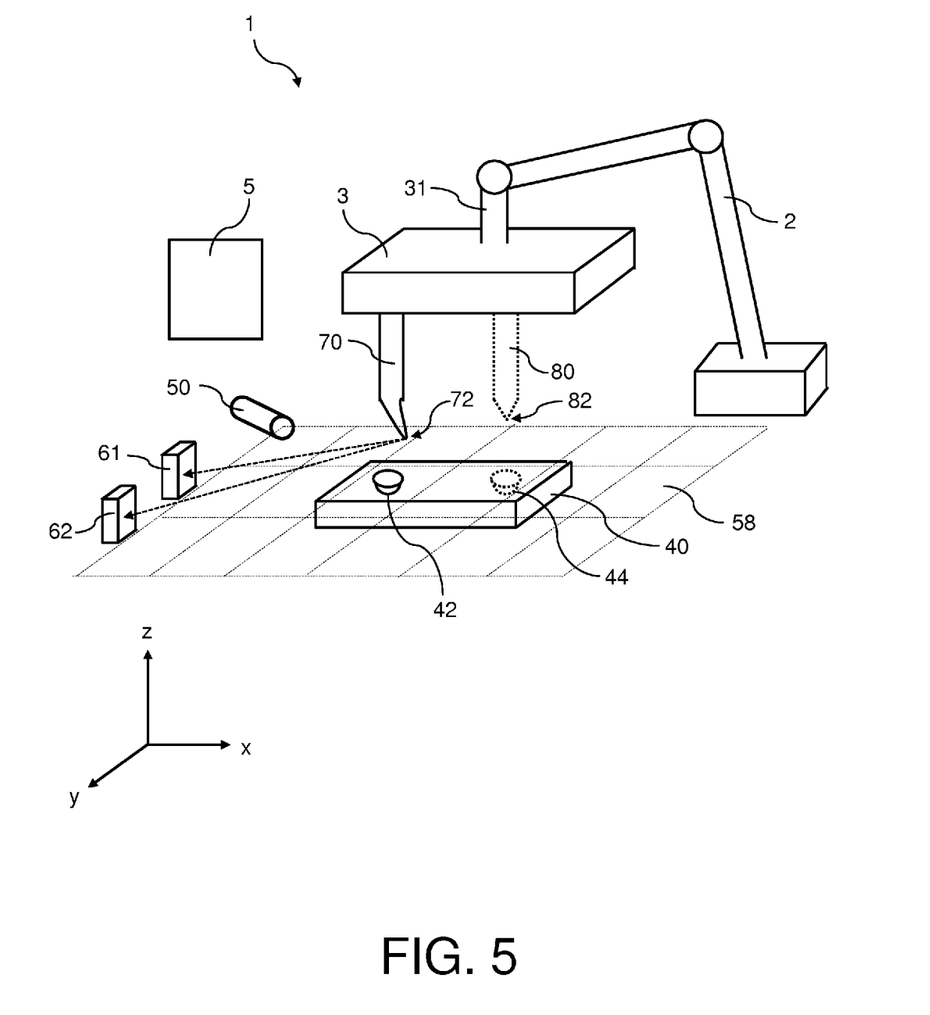
FIG. 5 is a perspective view of a sample processing apparatus according to one embodiment.

In some embodiments, the arrangement shown in FIG. 5 can be used to determine the lower end positions of multiple pipette tips. For example, the pipetting head 3 may be attached to a second pipette tip 80 that has a lower end 82. As shown in FIG. 5, the lower end 82 has a higher z-axis height than the lower end 72 of pipette tip 70, and thus when the lower end 72 intersects with the plane of laser light 58, lower end 82 is still located above the plane 58. After the position of lower end 72 has been identified, the robotic manipulator 2 may continue downward translation until the second lower end 82 intersects with the plane 58 and is illuminated. The illumination of lower end 82 is detected by detectors 61 and 62, and the position of lower end 82 can be calculated. When lower end 82 intersects with plane 58, first pipette tip 70 also intersects with the plane 58, and thus detectors 61, 62 will detect two illuminations: the first pipette tip 72 and the lower end 82 second pipette tip 80. The controller may be programmed to recognize that illumination of lower end 82 is the illumination of a second pipette tip, and illumination of first pipette tip 70 is the continued illumination of an object that was already identified. The continued illumination of the first pipette tip 70 may allow the controller to acquire more information about the rest of the pipette tip 70, including any deformities and irregularities that may be present on the pipette tip in locations other than the lower end 72. In this manner, a single, stationary laser source 50 may be used to identify the positions of multiple pipette tips. In one embodiment, the pipetting head is attached to a plurality of pipette tips, the robotic manipulator intersects all of the pipette tips through a plane of laser light by passing the tips through the plane, and information about the geometries of each pipette tip is received by the controller.

Once the position of the lower end of the pipette tip is determined, the controller may determine whether or not the position of the lower end is proper by comparing the position to the known length and geometry of regular, non-deformed pipette tips and/or the known position of the pipette channel to which the tip is attached. For example, the controller may determine whether the pipette tip is suitably near a central axis of the pipette channel or not, and take corrective action if needed. Thus, if a discrepancy over a threshold value exists, the system determines that the lower end is not in the proper location and may trigger a compensating action. In some embodiments, the controller may calculate a discrepancy between the "proper" position of the lower end of the pipette tip and the actual position of the lower end that was detected by the laser triangulation system. The proper position of the lower end is defined by the position the lower end would be at if the pipette tip were not deformed. The controller may then command the robotic manipulator to displace the pipetting head by a distance and direction that eliminates the discrepancy such that the lower end of the pipette tip is positioned properly for liquid handling actions. Thereafter, the pipetting head may then perform one or more sample handling operations using the pipette tip. In some embodiments, instead of displacing the pipette tip, the well plate or other vessel may be displaced to eliminate the discrepancy.

Figure 6:
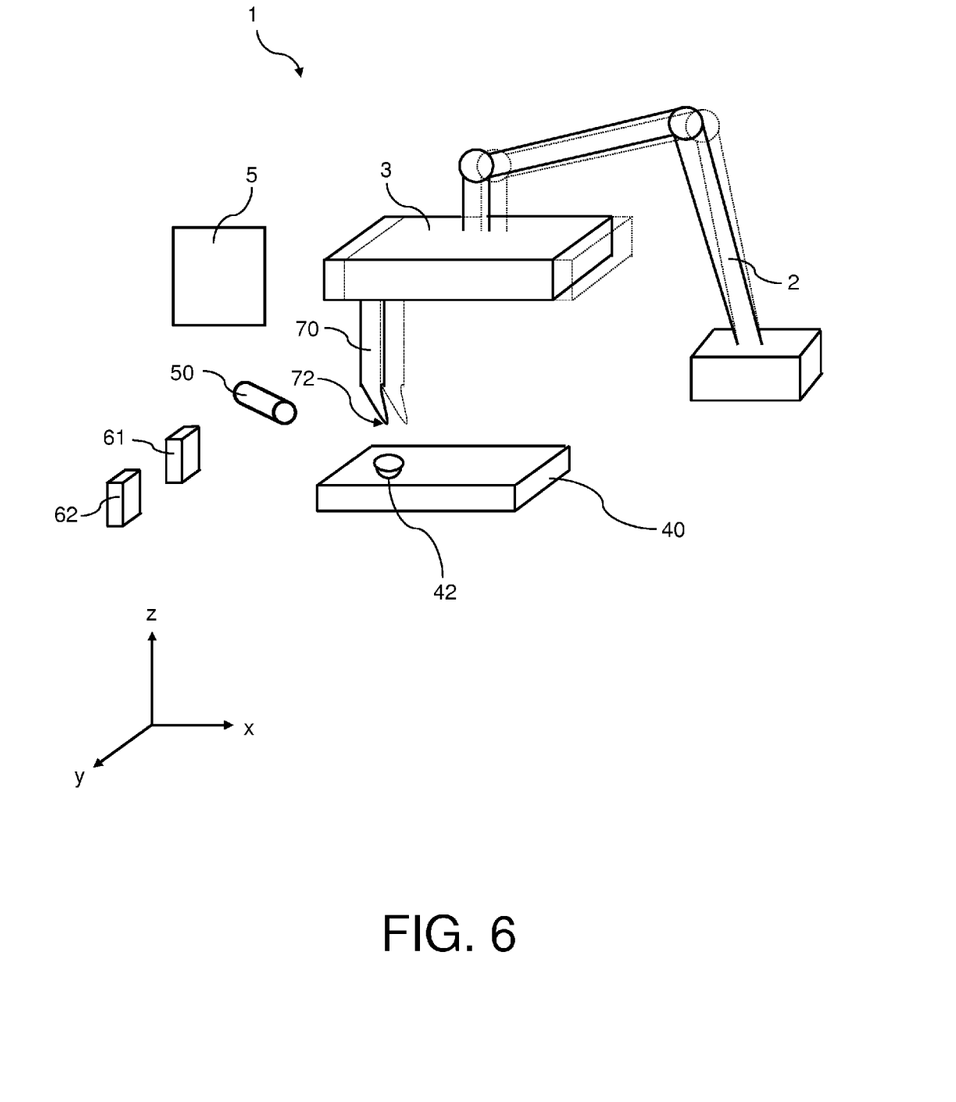
FIG. 6 is a perspective view of the sample processing apparatus depicted in FIG. 5 undergoing a compensating action according to one embodiment.

In one illustrative embodiment, FIG. 6 depicts the sample processing apparatus 1 undergoing a compensating action. Controller 5 commands the robotic manipulator 2 to shift the pipetting head 3 and place the lower end 72 in the proper position such that the lower end 72 is vertically aligned with the well 42 below. The laser triangulation system may be turned off during this time, or it may be used to verify that the compensating action has positioned the lower end 72 in the proper position.

In some embodiments, a compensating action may include ejecting the pipette tip and attaching a new pipette tip, e.g., where a determination is made that the tip is simply too deformed for proper use. In some embodiments, where more than one pipette tip is attached to the pipetting head, a compensating action may include disabling the dispenser in the pipetting head associated with the deformed pipette tip and carrying out sample handling operations with the remaining non-deformed pipette tips. In some embodiments, a compensating action may include contacting the lower end of the pipette tip against a surface to bend or otherwise displace the lower end back into a proper alignment such that the lower end is aligned with the longitudinal axis of the pipette tip. Alternatively or in addition to the aforementioned actions, the compensation action may include an alarm. The alarm may be auditory, visual, physical (e.g. a vibration or a shock), any combination thereof, or any other suitable type of alarm, as this aspect is not limited in this regard.

The controller 5 may have a user interface so that a user can interact with the controller and the sample processing apparatus 1. In one embodiment, the controller may include a computer system, which provides a user interface including a keyboard, mouse or other user pointing device, touch screen, display, printer and/or other components. In one embodiment, the user interface may include a graphical user interface (GUI) by which the user may receive information from, and input information to, the controller 5. The GUI may alert the user of a deformed pipette tip. The GUI may also enable the user to select a compensating action in response to detection of a deformed pipette tip. The user may set a default compensating action that the system carries out automatically in response to detection of a deformed tip such that a user need not select a compensating action each time a deformation is detected. The controller may keep track of the number of deformed tips and display a report through the GUI. A user may be permitted to alter and/or add to the information stored in the controller as desired, e.g., to provide comments regarding a specific batch number, to record processing conditions of a specific date, and so on. Information received by the controller can be stored in a database or other suitable storage medium for later reference or other use.

A user may also be able to program the sample processing apparatus or otherwise alter operating instructions used by the controller through the GUI, e.g., specifying the actions of the pipetting head, robotic manipulator; the volume of sample aspirated and/or dispensed, and/or other actions. The operator may additionally be able to program when the laser triangulation system is to be used, and what compensating actions should be performed. The user interface may additionally or alternatively comprise buttons, dials, or other non-GUI means that will be apparent to those of skill in the art.

Figure 7:
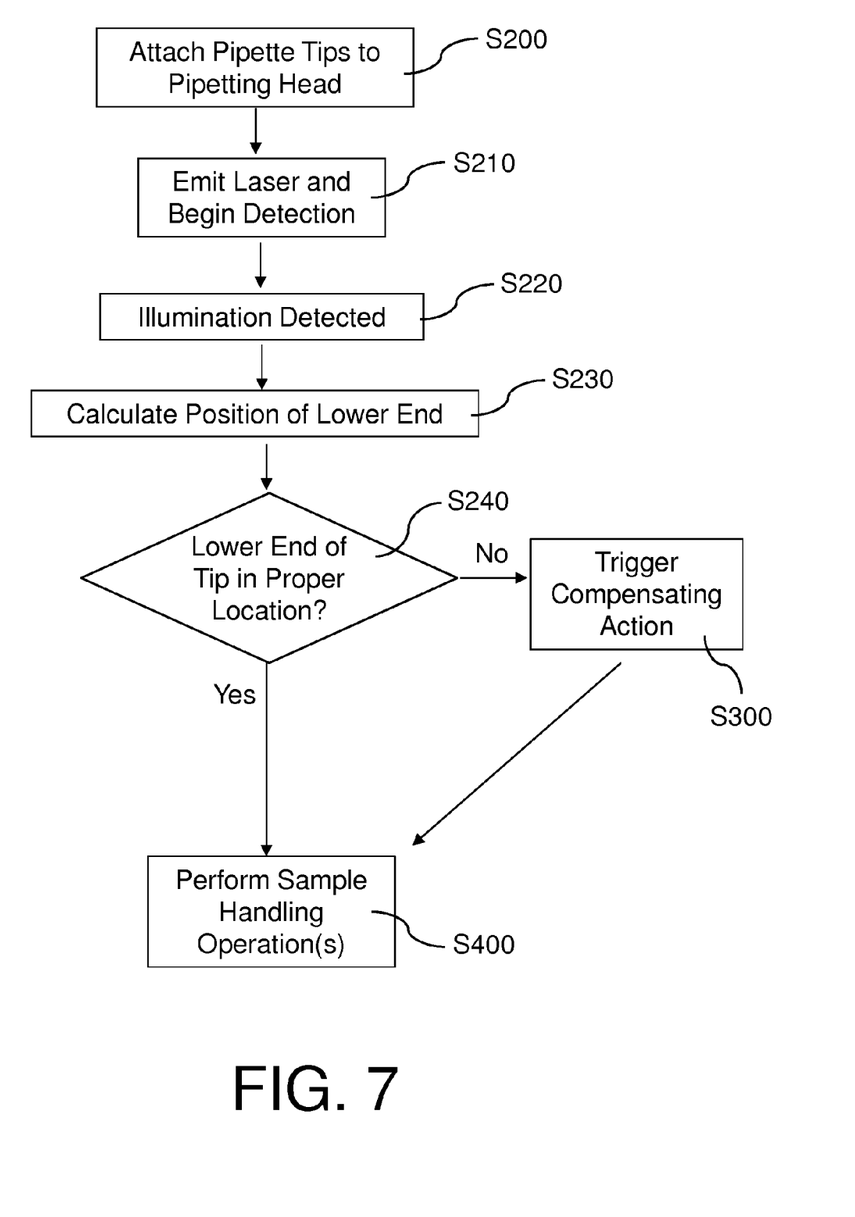
FIG. 7 is a block diagram of an operating procedure according to one embodiment.

One illustrative embodiment of an operating procedure of the sample processing apparatus is shown in FIG. 7. In step S200, the controller of the sample processing apparatus may direct a pipetting head to attach one or more pipette tips to the pipetting head. The controller may then command a laser source to emit a laser a detector to begin detection in step S210. When illumination is detected in step S220, the position of the lower end is calculated in step S230. The calculated "actual" position of the lower end is compared against the "proper" position in step S240. If the controller determines that the lower end is in the proper position, the system moves on to step S400 and performs one or more sample handling operations such as dispensing fluid into a well of a well plate. If the controller determines that the lower end is not in the proper position, the system proceeds to trigger a compensating action in step S300, and then proceeds to perform one or more sample handling operations in step S400.

The method described above is one of many possibilities for a sample processing apparatus with laser triangulation for detection of pipette tip deformities. A number of variations are also within the scope of the present invention and will be apparent to one of skill in the art.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method for determining pipette tip position, comprising:
   attaching a first pipette tip to a pipetting head, the first pipette tip having a first end for attaching to the pipetting head and a lower end that extends away from the pipetting head and the first end;
   using laser triangulation to locate a three-dimensional position of the lower end of the first pipette tip relative to a first reference point; and
   determining whether to compensate for the three-dimensional position of the lower end of the first pipette tip with a compensating action, wherein the determining comprises:
   i) calculating the three-dimensional position of the lower end of the first pipette tip; and
   ii) determining if there is a difference between the three-dimensional position of the lower end and a proper position of the lower end.

2. The method of claim 1, wherein the step of using laser triangulation includes:
   emitting a laser beam from a laser source toward the lower end of the first pipette tip;
   illuminating the lower end of the first pipette tip with the laser beam;
   detecting the illumination of the lower end using a detector; and
   calculating the three-dimensional position of the lower end using a controller.

3. The method of claim 1, further comprising: moving the pipetting head to position the lower end of the first pipette tip at the proper position of the lower end in response to determining that there is a difference between the three-dimensional position of the lower end of the first pipette tip and the proper position of the lower end.

4. The method of claim 3, wherein, in the proper position, the lower end of the first pipette tip is vertically aligned with an opening of a vessel.

5. The method of claim 4, further comprising performing a sample handling operation with the pipetting head and the first pipette tip.

6. The method of claim 5, wherein the sample handling operation comprises at least one of filtering, aspirating, dispensing, centrifuging, cell plating, or electrophoretic separation.

7. The method of claim 1, further comprising:
   attaching a second pipette tip to the pipetting head, the second pipette tip having a second lower end that faces away from the pipetting head;
   using laser triangulation to locate a three-dimensional position of the second lower end of the second pipette tip relative to a second reference point; and
   determining whether to compensate for the three-dimensional position of the second lower end of the second pipette tip with a compensating action, wherein the determining comprises:
   i) calculating the three-dimensional position of the second lower end of the second pipette tip; and
   ii) determining if there is a difference between the three-dimensional position of the second lower end of the second pipette tip and a proper position of the second lower end of the second pipette tip.

8. The method of claim 1, further comprising: ejecting the first pipette tip in response to determining that there is a difference between the three-dimensional position of the lower end of the first pipette tip and the proper position of the lower end.

9. The method of claim 1, further comprising: disabling liquid handling function of the first pipette tip in response to determining that there is a difference between the three-dimensional position of the lower end of the first pipette tip and the proper position of the lower end.

10. The method of claim 1, further comprising: attaching a plurality of pipette tips to the pipetting head, each of the plurality of pipette tips having a lower end that faces away from the pipetting head; using laser triangulation to locate three-dimensional positions of the lower ends of the plurality of pipette tips relative to a plurality of defined reference points; and determining whether to compensate for the three-dimensional positions of the lower ends of the plurality of pipette tips with a compensating action, wherein the determining comprises:
   i) calculating the three-dimensional positions of the lower ends of the plurality of pipette tips; and
   ii) determining if there is a difference between the three-dimensional positions of the lower ends of the plurality of pipette tips and a proper position of the lower end of the plurality of pipette tips.

11. A sample handling apparatus, comprising:
   a pipetting head adapted to hold a first pipette tip and allow for movement of a liquid sample relative to the first pipette tip, the first pipette tip having a lower end;
   a laser triangulation system constructed and arranged to locate a three-dimensional position of the lower end of the first pipette tip relative to the pipetting head; and
   a controller constructed and arranged to: i) calculate the three-dimensional position of the lower end of the first pipette tip relative to the pipetting head; ii) calculate if there is a difference between the three-dimensional position of the lower end of the first pipette tip and a proper position of the lower end of the first pipette tip; and iii) operate the pipetting head to perform a compensating action to compensate for the three-dimensional position of the lower end of the first pipette.

12. The sample handling apparatus of claim 11, wherein the laser triangulation system comprises a first laser source and a first detector.

13. The sample handling apparatus of claim 12, wherein the laser triangulation system further comprises a second detector.

14. The sample handling apparatus of claim 12, wherein the controller is constructed and arranged to receive information from the first detector.

15. The sample handling apparatus of claim 12, wherein the controller is constructed and arranged to receive information from the first laser source.

16. The sample handling apparatus of claim 11, further comprising a robotic manipulator adapted to manipulate a position of the pipetting head.

17. The sample handling apparatus of claim 16, wherein the controller is constructed and arranged to control the robotic manipulator.

18. The sample handling apparatus of claim 11, wherein the compensating action comprises a movement of the pipetting head to position the lower end of the first pipette tip at the proper position.

19. The sample handling apparatus of claim 18, wherein, in the proper position, the lower end of the first pipette tip is vertically aligned with an opening of a vessel.

20. The sample handling apparatus of claim 11, wherein the pipetting head is configured to hold a plurality of pipette tips, the plurality of pipette tips each having a lower end that faces away from the pipetting head;

the laser triangulation system is constructed and arranged to locate a three-dimensional position of the lower end of each of the plurality of pipette tips relative to the pipetting head; and the controller is constructed and arranged to:
  i) calculate the three-dimensional position of the lower ends of each of the plurality of pipette tips relative to the pipetting head;
  ii) determine if there is a difference between the three-dimensional position of the lower end of each of the plurality of pipette tips and a proper position of the lower end of each of the plurality of pipette tips; and
  iii) operate the pipetting head to perform a compensating action to compensate for the three-dimensional position of the lower end of at least one of the plurality of pipette tips.

\* \* \* \* \*